United States Patent
Menon

(10) Patent No.: US 9,648,872 B2
(45) Date of Patent: May 16, 2017

(54) WATER DISPERSIBLE GRANULE COMPOSITION

(71) Applicant: Deepak Shah, Juhu, Mumbai, Maharashtra (IN)

(72) Inventor: Ramdas Puthenveetll Kunjukrishna Menon, Navi Mumbai (IN)

(73) Assignee: Deepak Pranjivandas Shah (IN)

( * ) Notice: Subject to any disclaimer, the term of this patent is extended or adjusted under 35 U.S.C. 154(b) by 0 days.

(21) Appl. No.: 14/626,115

(22) Filed: Feb. 19, 2015

(65) Prior Publication Data

US 2015/0230471 A1 Aug. 20, 2015

(30) Foreign Application Priority Data

Feb. 19, 2014 (IN) .......................... 574/MUM/2014

(51) Int. Cl.
*A01N 25/28* (2006.01)
*A01N 49/00* (2006.01)
*A01P 7/04* (2006.01)
*A01P 3/00* (2006.01)
*A01P 13/00* (2006.01)

(52) U.S. Cl.
CPC .................................. *A01N 25/28* (2013.01)

(58) Field of Classification Search
None
See application file for complete search history.

(56) References Cited

U.S. PATENT DOCUMENTS

| | | | |
|---|---|---|---|
| 4,936,901 A * | 6/1990 | Surgant, Sr. ........... | A01N 25/28 504/133 |
| 6,232,049 B1 * | 5/2001 | Nair ..................... | G03C 1/7614 430/350 |
| 6,358,520 B1 * | 3/2002 | Lo ......................... | A01N 25/28 264/4.1 |
| 6,419,942 B1 | 7/2002 | Lo et al. | |
| 8,652,498 B2 | 2/2014 | Shah | |
| 2010/0267563 A1 | 10/2010 | Pedroni et al. | |

FOREIGN PATENT DOCUMENTS

| WO | WO2013066943 | 5/2013 |
|---|---|---|
| WO | WO2013066950 | 5/2013 |

* cited by examiner

*Primary Examiner* — Abigail Fisher

(74) *Attorney, Agent, or Firm* — Veritay Group, IP; Susan B. Fentress

(57) ABSTRACT

A water dispersible granular composition comprising: i. microcapsules comprising of: a. at least one agrochemical active ingredient encapsulated within a polymeric shell wall; and, wherein the agrochemical active ingredient has a water solubility of less than 100 mg/liter; and, b. polyvinyl alcohol with a molecular weight of from 15,000 to 21,000, a degree of hydrolysis of from 87% to 89% and a viscosity of from 3.5 cps to 4.5 cps; ii. a filler base comprising of: a. at least one water insoluble filler; and b. at least one water soluble suspension adjuvant; and, iii. at least one agrochemical excipient.

13 Claims, No Drawings

WATER DISPERSIBLE GRANULE COMPOSITION

CROSS REFERENCE TO THE RELATED APPLICATIONS

This application is a non provisional application which claims foreign priority under 35U.S.C. § 119to an Indian patent application 574/MUM/2014 filed on Feb. 19, 2014 in India (hereby specially incorporated by reference).

FIELD OF THE INVENTION

The present invention relates to method of treating plants with a novel water dispersible granular composition comprising microcapsules of one or more agrochemical active ingredients. More particularly, the invention relates to a water dispersible granular composition comprising microcapsules, wherein the microcapsules include at least one agrochemical active ingredient with a water solubility of less than 100 mg/liter, encapsulated within a polymeric shell wall and polyvinyl alcohol. The water dispersible granular composition further includes a filler base comprising at least one water insoluble filler; at least one water soluble suspension adjuvant and at least one agrochemical excipient.

BACKGROUND OF THE INVENTION

In describing the embodiments of the invention, specific terminology is chosen for the sake of clarity. However, it is not intended that the invention be limited to the specific terms so selected and it is to be understood that each specific term includes all technical equivalents that operate in a similar manner to accomplish a similar purpose.

Several agrochemical active ingredients used for long periods of time are often used at high dosages for countering pests and diseases, which is a constant burden on the environment. Active ingredients which have a low solubility in water and are highly soluble in water-immiscible solvents are typically formulated as emulsifiable concentrates, microemulsions or capsulated suspensions.

Emulsifiable concentrates often perform very well, are stable, and offer good efficacy but pose a severe risk and threat to the environment in terms of toxicity.

Microcapsules or capsulated suspensions which encapsulate the active ingredient within a polymeric wall offer particular advantages. The encapsulation of the pesticidal active ingredients makes the formulation safe for the applicator or the end user. Since the pesticide is enclosed in a polymeric shell wall, the user is not directly exposed to the chemical. The use of an encapsulated composition ensures activity of the active ingredient over an extended period of time, since the active ingredient is released continuously into the environment rather than in one single dose. Microencapsulated pesticides of the controlled release or the quick release types, are usually sold in the form of aqueous suspensions of the microcapsules. However, microcapsules or capsulated suspensions are found to be unstable over broad temperature ranges. Besides, they exhibit a high tendency of crystallization of the active ingredients. Further, capsulated suspensions suffer from disadvantages of higher packaging costs.

Due to these drawbacks, it is advantageous to provide such microencapsulated compositions in a dry form, such as water dispersible granules rather than as aqueous suspensions. Dry formulations can be prepared with a relatively high loading of the pesticide, are easier to remove from the containers and produce less contamination in the environment. Furthermore, dry formulations are preferred as they can be stored over longer periods of time and do not require the simultaneous storage and transport of large volumes of water.

Dry forms such as water dispersible granules are particularly preferred as they can be stored for over longer durations, over wide extremes of temperature, without destroying the stability of the formulation. In addition, it is convenient to provide a solid formulation of microencapsulated pesticides, which is water dispersible and can be readily mixed with water to produce sprayable materials. Further, shipping costs are reduced since inclusion of solvents, water carriers and water-based flowable pesticide formulations is eliminated.

Water dispersible granules of microcapsules within polyurea shell wall are known. U.S. Pat. No. 6,419,942 discloses water dispersible granule composition of microcapsules encapsulating an active ingredient. It is observed that these prior art granules are difficult to dry and choke the nozzle. It is observed that the formulation forms lumps in the spray suspension, when the formulation is diluted in water. Also, these granules demonstrate average biological efficacy and poor suspensibility, particularly upon accelerated storage. U.S. Pat. No. 6,919,942 is also silent on the physical properties of the formulation.

It is understood that a composition may demonstrate satisfactory initial dispersibility but may not necessarily demonstrate good suspensibility. Thus, it is always desirable to have a water dispersible granule formulation that not only disperses spontaneously, but also remains suspended upon dilution for a continuous period of time. There is a further need to develop a water dispersible granule formulation of microcapsules which is effective for an extended period of time, with reduced dosage of application.

SUMMARY OF THE INVENTION

It has now been determined that a method of treating plants with a water dispersible granule composition comprising microcapsules of an agrochemical active ingredient, helps reduce active dosage applied while giving effective control over pests and diseases. Surprisingly, the inventors have developed a water dispersible granular composition comprising microcapsules of at least one agrochemical active ingredient, wherein the composition demonstrated surprisingly higher efficacy at significantly reduced dosages of application of the active ingredient. It was also observed that the composition exhibited good physical and chemical properties, good release properties, enhanced stability even at extended storage under higher temperatures. The water dispersible granular composition comprises microcapsules; wherein the microcapsules include at least one agrochemical active ingredient with a water solubility of less than 100 mg/liter, encapsulated within a polymeric shell wall and polyvinyl alcohol. The polyvinyl alcohol has a molecular weight of from 15,000 to 21,000, a degree of hydrolysis of from 87% to 89% and a viscosity of from 3.5 cps to 4.5 cps. The water dispersible granular composition further comprises a filler base which includes at least one water insoluble filler; at least one water soluble suspension adjuvant selected from the group consisting of water soluble carbohydrates and polyvinyl pyrolidone and at least one agrochemical excipient.

According to another embodiment, the invention further relates to a process of preparation of the water dispersible granular composition comprising the microcapsules.

According to another embodiment, the invention further relates to a method of treatment of plants using water dispersible granular composition comprising the microcapsules.

DETAILED DESCRIPTION OF THE INVENTION

In describing the embodiments of the invention, specific terminology is resorted for the sake of clarity. However, it is not intended that the invention be limited to the specific terms so selected and it is to be understood that each specific term includes all technical equivalents that operate in a similar manner to accomplish a similar purpose.

The invention relates to a novel water dispersible granular composition comprising microcapsules wherein the microcapsules include at least one agrochemical active ingredient encapsulated within a polymeric shell wall; and polyvinyl alcohol. The agrochemical active ingredients have a water solubility of less than 100 mg/liter. The polyvinyl alcohol has a molecular weight of from 15,000 to 21,000, a degree of hydrolysis of from 87% to 89% and a viscosity of from 3.5 cps to 4.5 cps. The water dispersible granular composition further comprises a filler base. The filler base includes, at least one water insoluble filler, at least one water soluble suspension adjuvant selected from the group consisting of water soluble carbohydrates and polyvinyl pyrolidone and at least one agrochemical excipient. The invention also relates to a method of treatment of plants, comprising applying to the plant, plant propagation material or locus thereof, a water dispersible granule composition comprising the above microcapsules and the filler base.

When these water dispersible granules come in contact with an aqueous medium, they disintegrate immediately to release the individual microcapsules of the encapsulated material, and remain dispersed and suspended uniformly throughout the aqueous medium.

Surprisingly, the inventors have determined that the composition of the water dispersible granule of the present invention display enhanced efficacy at reduced dosage of application of the composition as compared to other prior art compositions of water dispersible granules, microcapsules or emulsifiable concentrates. It was further observed that the water dispersible granular composition comprising the microcapsules encapsulating the active ingredient, eliminates the use of any anti-settling or anti-caking agents while exhibiting excellent storage stability, and excellent physical properties of suspension and dispersion when added to water.

The microcapsules containing the agrochemical active ingredient used in this invention may be prepared by any of the known microencapsulation techniques. Various methods of encapsulation are known such as coacervation encapsulation, interfacial condensation polymerization and fluid bed coating. According to an embodiment of the invention, the microcaspule shell wall is formed of polyamides, polyesters, polysulfonamide, polyurethanes, polythioester, polyphosphonamide, polyiminourea, polyurea, polysiloxane, aminoplast resins, polycarbonates or mixtures thereof. Preferably, according to an embodiment of the invention, the shell wall is a polyurea shell wall formed by the interfacial condensation polymerization reaction, between an isocyanate and an amine wherein the amine can be a diamine or a polyamine.

Briefly, microencapsulation via interfacial condensation polymerization reaction involves encapsulating one or more agrochemical active ingredients within a polymeric shell wall. The microencapsulation process typically involves preparation of an organic phase or an oil phase and an aqueous phase. At first, the oil or organic phase is prepared by mixing the agrochemical active ingredient, and at least one first monomer, which will become polymerized at the organic/aqueous phase interface to form a polymeric shell for the microcapsule. Alternatively, the process may be varied by performing a milling process to reduce the particle size of the active ingredient, after the compound has been suspended in the organic phase.

The agrochemical active ingredient is a water insoluble active ingredient with a solubility of less than 100 mg/liter in water at 20° C., and has a high solubility in water-immiscible solvents. The inventors have surprisingly developed an excellent water dispersible granule composition for actives, particularly those having a water solubility less than 100 mg/liter in water. It is observed that the compositions of the present invention, for these water insoluble actives, demonstrates excellent physical properties. Active ingredients with higher water solubilities do not demonstrate any enhancement in properties and in fact, it is observed that for certain actives, the composition of the present invention results in a deterioration of their physical properties. The active ingredient can be a low melting active ingredient or a liquid active ingredient. The low-melting active ingredient should be chemically stable in the molten phase and amenable to aqueous microencapsulation chemistry. The agrochemical active ingredient is suitably a liquid at ambient temperature of from 5 degree celcius to 50 degree celcius and may be utilized per se when it is in a liquid form. The agrochemical active ingredient can also be a solid active ingredient which can be rendered in a liquid form by dissolving or suspending it in an appropriate solvent. For instance, actives such as Lambda-cyhalothrin and Propaquizofop which are solids at ambient temperature, can be converted into a liquid form, by warming, or in admixture with suitable liquid emulsfiers, solvent or other non aqueous liquids.

According to an embodiment, the agrochemical active ingredient includes insecticides, fungicides, herbicides, acaricides, nematicides, rodenticides, pheromones, plant growth regulators and mixtures thereof.

According to an embodiment, the agrochemical active ingredient includes Halfenprox, Allethrin, Deltamethrin, Bifenthrin, Gamma-Cyhalothrin, Acrinathrin, Alpha-Cypermethrin, Cyhalothrin, Lambda-Cyhalothrin, Flumetralin, Fluotrimazole, Tefluthrin, Etofenprox, Fenpyroximate, Spirodiclofen, Benfluralin, Tolfenpyrad, Fenazaquin, Chlorfenapyr, Fluazinam, Propargite, Trifluralin, Bioresmethrin, Quizalofop-Ethyl, Fenpropathrin, Buprofezin, Propaquizafop, Chlorothalonil, Chlorpyrifos, Fenpropimorph, Fenvalerate, Tau-Fluvalinate, Beta-Cyfluthrin, Flufenprox, DDT, Hydramethylnon, Cyfluthrin, Acequinocyl, Ethalfluralin, Pyridaben, Dienochlor, Aldrin, Bromoxynil Octanoate, Ioxynil Octanoate, Tetrasul, Zeta-Cypermethrin, Silthiofam, Lufenuron, Heptachlor, Etoxazole, Prothiofos, Tralomethrin, Methoxychlor, Alpha-Endosulfan, Aclonifen, Alanycarb, Spiromesifen, Dinocap, Indoxacarb, Permethrin, Chlorthal-Dimethyl, Meptyldinocap, Chlornitrofen, Chlomethoxyfen, Endosulfan, Ethiozin, Fluacrypyrim, Diclofop-Methyl, Cyhalofop-Butyl, Quintozene, Cyflufenamid, Oxadiazon, Haloxyfop-Etotyl, Aramite, Cloquintocet-Mexyl, Quizalofop-P-Ethyl, Trifloxystrobin, Metofluthrin, Metamifop, Tolciofos-Methyl, Dicofol, Fenchlorazole-Ethyl, Fluchloralin, Tolylfluanid, Binapacryl, Fentin Hydroxide, Dichlofluanid, Tecnazene, Penthiopyrad, Dithiopyr, Captafol, Phosalone, Pyridate, Chloropropylate, Phoxim, Pyriofenone, Flubenzimine, Haloxyfop, Imibenconazole, Fluorodifen, Mcpa-Thioethyl, Fentrazamide, Tebufenpyrad, Leptophos, Procymidone, Fenclorim, Fluenetil, Chlorpyrifos-Methyl, Chlorfenson, Camphechlor, Picoxystrobin, Quizalofop-P-Tefuryl, Vinclozolin, Tri-Allate, Fenthion, Pyrazophos, Azinphos-Ethyl, Dinoterb, Bioallethrin, Isofetamid, Halacrinate, Tralkoxydim, Azoxystrobin, Fenoxycarb, Haloxyfop-P-Methyl, Prallethrin, Carfentrazone-ethyl, Pendimethalin, Climbazole, Benfuracarb, Pentanochlor, Lindane, Anilofos, Isoxapyrifop, Chlorobenzilate, Isomethiozin, Penflufen, Barban, Phenthoate, Pirimiphos-Methyl, Flamprop-M-Isopropyl, Iprodione, Halofenozide, Parathion, Mepronil, Cyprodinil, Bupirimate, Prosulfocarb, Sedaxane, Difenoconazole, Fluopyram, Thiobencarb, Quinalphos, Butathiofos, Dimepiperate, Mefenpyr, Oxabetrinil, Trietazine, Fenpyrazamine, Flurochloridone, Isofenphos, Orbencarb, Prochloraz, Profoxydim, Azinphos-Methyl, Dimethomorph, Spinetoram, Spirotetramat, Benzoximate, Fenothiocarb, Metconazole, Benalaxyl-M, Chlorbromuron, Tebuconazole, Flurenol, Flusilazole, Chlobenthiazone, Bromuconazole, Plifenate, Parathion-Methyl, Edifenphos, Flufenacet, Diazinon, Methabenzthiazuron, Linuron, Bensulfuron-Methyl, Triadimefon, Fluothiuron, Penconazole, Orysastrobin, 2,5-Dichlorobenzoic Acid Methyl Ester, Propisochlor, Propanil, Fenfuram, Mexacarbate, Pyridafenthion, Fluroxypyr-Meptyl, Oxadiargyl, Flucythrinate, Isopyrazam, Bensultap, Fluazifop-P-Butyl, Fluazifop-Butyl, Cyphenothrin, Prodiamine, Fenbutatin Oxide, Picolinafen, Quinoxyfen, Cinidon-Ethyl, Transfluthrin, Tetradifon, Bromoxynil Heptanoate, Bifenox, Bromopropylate, Amisulbrom, Tetramethrin, Clodinafop-Propargyl, Imiprothrin, Beta-Cypermethrin, Kadethrin, Cypermethrin, Empenthrin, Phenothrin, Resmethrin, Dimethrin, Furethrin, Cycloprothrin, Profluthrin, Cyhalofop and mixtures thereof. The above list is exemplary and other pesticidal active ingredients which have solubilities of less than 100 mg/l in water and are miscible in water immiscible solvents are also within the scope of the invention.

According to an embodiment, the agrochemical active ingredient includes one or more of aryloxyphenoxypropionic herbicides. The aryloxyphenoxypropionic herbicides include chlorazifop, clodinafop, clofop, cyhalofop, diclofop, fenoxaprop, fenoxaprop-P, fenthiaprop, fluazifop, fluazifop-P, haloxyfop, haloxyfop-P, isoxapyrifop, kuicaoxi, metamifop, propaquizafop, quizalofop, quizalofop-P and trifop.

According to an embodiment, the agrochemical active ingredient includes pyrethroids. The pyrethroids can be selected from one or more of permethrin, fenvalerate, esfenvalerate, cypermethrin, alpha-cypermethrin, deltamethrin, fenpropathrin, fluvalinate, flucythrinate, cyfluthrin, acrinathrin, tralomethrin, cycloprothrin, lambda cyhalothrin, teflu-thrin, bifenthrin, transfluthrin, zeta-cypermethrin, etofenprox and flufenprox.

The agrochemical active ingredient particularly includes one or more of lambda cyhalothrin, cypermethrin, bifenthrin and permethrin. According to an embodiment, the agrochemical active ingredient is lambda cyhalothrin.

The concentration of the agrochemical active ingredient should be at least sufficient to be pesticidally effective and ranges upto about 60% by weight of the water dispersible granules. A suitable concentration range is 5%-60% by weight.

According to an embodiment, the first monomer employed in the organic phase includes isocyanates such as polymethylenepolyphenyleneisocyanate (PMPPI), hexmethylenediisocyanate (HMDI), isophoronediisocyanate (IPDI) or 4,4' methylenebis(cyclohexyl isocyanate) and/or trimers of HMDI or IPDI and the like, isomers of tolylene diisocyanate, isomers and derivatives of phenylene diisocyanate, isomers and derivatives of biphenylene diisocyanates, methylene diphenyl diisocyanate (MDI), polymeric polyisocyanates, biurets and blocked polyisocyanates or mixtures thereof.

The concentration of the isocyanate(s) and the ratio where more than one isocyanate is used, is chosen so as to obtain the desired release rate profile for the particular application. In general, the isocyanate(s) will comprise from about 0.3 to about 20%, more suitably from about 0.5 to about 15%, even more suitably from about 1% to about 25% and most suitably from about 10% to about 20%, by weight of the microcapsule.

The organic phase can also include other optional components such as surfactants, cross-linking agents, permeability enhancing agents such as castor oil, and a suspended particulate well-dispersed ultraviolet protectant material such as titanium dioxide and/or zinc oxide. The ultraviolet protectant material is included in the organic phase, if the agrochemical active ingredient is sensitive to ultraviolet light. The oil phase can also have a solvent to render a solid active ingredient in a liquid form.

Solvents which can be used to dissolve the solid active ingredient, if necessary, include but are not limited to aromatic chlorinated hydrocarbons, chlorinated maleic hydrocarbons, ketones, long chain esters and mixtures thereof, (commercially available as Solvesso 100, Solvesso 150, Solvesso 200, Solvesso 150ND, Solvesso 200ND, Aromatic 200, Hydrosol A 200, Hydrosol A 230/270, Caromax 20, Caromax 28, Aromat K 150, Aromat K 200, Shellsol A 150, Shellsol A 100, Fin FAS-TX 150, Fin FAST-TX 200, Xylene, Cyclohexane, Cyclopentane, Pentane, Hexane, Heptane, octane, nonane, decane, isooctane, benzene, 2-Methylpentane, 3-Methylpentane, 2-Methyl hexane, 3-Methylhexane, 2-methylbutane, 2,3-Dimethylpentane, Methycyclopentane, Methylcyclohexane, 2,4 Dimethylpentane, aromatics such as benzene, toluene, and the like; cyclohexane, 1-Pentene, 2-Pentene, 1-Hexene, 1-Heptene, Cyclohexene, Ethylvinylether, Propylether, Isopropylether, petroleum distillates, petroleum ether, and the like, Butylvinylether, Butylethylether, 1,2-Epoxybutane, Furan, Tetrahydropyran, 1-Butanal, 2-methylpropanal, 2-Pentanone, 3-Pentanone, Fluorbenzene, Hexafluorobenzene, Ethylformate, Propylformate, Isopropylformate, Ethylacetate, Methylacrylate, Ethylacrylate, Methyl-methacrylate, Dichloromethane, Tetramethylsilane, substituted aromatics such as chlorobenzene, benzaldehyde, xylenes, and the like and mixtures thereof. However, those skilled in the art will appreciate that it is possible to utilize other solvents known in the art without departing from the scope of the invention. The solvents are present in a concentration range of from 5% to 15% by weight of the total composition.

The aqueous phase is prepared by mixing water, Polyvinyl alcohol, and optionally surfactants or emulsifiers, if required. Polyvinyl alcohol is usually sold in a solid form with wide variations in molecular weight and degree of hydrolysis. The polyvinyl alcohol is added in an amount sufficient to enhance the stability of the microcapsules. Particularly, polyvinyl alcohol of lower molecular weight or lesser degree of hydrolysis, which are more water-soluble, are preferred. According to an embodiment, the polyvinyl alcohol used in the composition has a molecular weight of from 15,000 to 21,000, a degree of hydrolysis of from 87% to 89% and a viscosity of from 3.5 cps to 4.5 cps. Commercially, the polyvinyl alcohols are available as Gohsenol GL-03. The aqueous phase can also include other polymers, depending on the type of polymer wall that is desired.

According to an embodiment, the other polymer can be selected from one or more of ethylene/maleic anhydride copolymers, methyl vinyl ether-maleic anhydride copolymer, water soluble polyesters, copolymers and homopolymers of acrylic acids and polyvinyl pyrrolidone.

The amount of Polyvinyl alcohol used in the aqeuous phase is in a concentration of from 2% to 20% by weight.

The surfactants that can be employed in the organic phase or the aqueous phase include one or more of sodium dodecyl benzene sulphonates, naphthalene sulfonates, alkyl naphthalene sulfonate condensate (Terrsperse 2020), ethoxylated alkylaryl phosphate esters, styrene acrylic polymers, block copolymers of polyalkylene glycol ether and hydroxystearic acid, ethoxylated alcohols, ethoxylated tristyrlphenols, etho-propoxylated tristyrlphenols, etho-propoxylated block copolymers and alkoxylated triglycerides. Commercially, dodecyl benzene sulphonates available as Rhodacal and AGROSURF; ethoxylated alkylaryl phosphates ester available as Rhodafac; alkyl naphthalene sulfonate formaldehyde is available as TERSPERSE 2425 and Daxad 11; and naphthalene sulfonates available as TAMOL FBP1 and PROPOL DSN.

The non-ionic surfactants that can be used in the organic phase include one or more of polyalkylene glycol ether or ethylene oxide-propylene oxide copolymer surfactants sold under the trade names Atlas G5000 and TERMUL 5429. Commercially, block copolymers of polyethylene glycol ether and hydroxystearic acid are available as TERMUL 2510, Arlacel P135, Hypermer 8261, Hypermer B239, Hypermer B261, Hypermer B246sf, Solutol HS 15; etho-propoxylated tristyrlphenols are available as Soprophor 7961P, Soprophor TSP/461, Soprophor TSP/724; alkoxylated triglycerides commercially available as Croduret 40, Etocas 200, Etocas 29 and Rokacet R26 and ethoxylated alcohols are commercially available as CHEMONIC OE-20. Other anionic surfactants which have been found to be useful include taurate surfactants like sodium N-cyclohexyl-N-palmitoyl taurate, sodium N-methyl-N-oleoyl taurate, respectively, sold under the tradenames, Igepon CN-42, Igepon T-33, T-43, T-51, T-73, T-77, and T-74 by GAF Corporation, Chemical Products, New York, N.Y., 10020. Sodium N-methyl-N-oleoyl taurate is also available under the tradename "Adinol" from Croda Chemicals, Ltd., England. Preferred for use herein is sodium N-methyl-N-oleoyl taurate.

Suitable surfactants include polyethylene glycol ethers of linear alcohols, ethoxylated nonylphenols, block copolymers of propylene oxide and ethylene oxide. In general, the range of surfactant concentration used in the organic phase or the aqueous phase is from 0.01% to about 10% by weight, but higher concentrations of surfactant may also be used, depending on the active ingredient.

The organic phase is then added to an aqueous phase with high shear or agitation or with stirring, forming a dispersion or emulsion of organic phase droplets in the aqueous phase. A suitable dispersing means is employed to disperse the organic phase in the aqueous phase. Selection of the dispersion process and apparatus will depend upon the desired particle size of the ultimate product to be produced. The dispersion is then subjected to conditions such as agitation or heating so as to cause the monomer or monomers contained in the organic phase droplets to polymerize at the interface between the organic and aqueous phases, forming shells of polymer around the droplets. The reaction temperature is generally in the range from about 20° C. to about 80° C.

A second monomer is then added to the dispersion or emulsion which is then stirred and cooled to room temperature. In the situation where approximately equimolar amounts of isocyanate and amino groups are present, the reaction temperature is preferably from about 40° C. to about 65° C. and even more preferably from about 50° C. to about 60° C.

The polymerization reaction is continued for around 2 hours, wherein a catalyst is optionally added to the dispersion slowly under shear. The pH of the dispersion is neutralized depending on the active ingredient and depending on the type of the shell wall polymer. The result is an aqueous suspension which is a two-phase system, wherein the microcapsules are suspended in an aqueous or a continuous phase liquid.

According to an embodiment, the second monomer employed includes diamines or polyamines or mixtures thereof. The monomers include compounds which are soluble in the aqueous phase. Aliphatic or alicyclic primary or secondary diamines or polyamines such as ethylene-1,2-diamine, diethylenetriamine, triethylenetetramine, bis-(3-aminopropyl)-amine, bis-(2-methylaminoethyl)-methylamine, 1,4-diaminocyclohexane, 3-amino-1-methylaminopropane, N-methyl-bis-(3-aminopropyl)amine, 1,4-diamino-n-butane, propylene 1,3-diamine, tetramethylene diamine, pentamethylene diamine, 1,6-hexamethylene diamine, triethylene diamine, 1,6-diamino-n-hexane and tetraethylenepentamine and mixtures thereof are suitably used. Polyethyleneimines are also suitable. Diamines and polyamines, usually selected as water soluble per se or in-water soluble salt form, are polymethylene diamines, phenylene diamine, toluene diamine and piperazine.

Particularly suitable amines are the polyfunctional amines which have a functionality greater than 2 but less than 3 and which may provide a degree of cross-linking in the shell wall. The polyfunctional amines should be in a water soluble salt form. Suitable examples of polyfunctional amines which may be used include 1,3,5-benzene triamine trihydrochloride, 2,4,6-triamino toluene trihydrochloride, 1,3,6-triaminonaphthalene, 3,4,5-triamino-1,2,4-triazole, melamine, 2,4,5,8-tetramino anthraquinone, propylenediamine, isopropylenediamine, ethenediamine, triethylenetetraamine, bix-hexamethylenetriamine, polyalkylene polyamines such as pentaethylene hexamine, and the like. The amines may be used alone or in combination with each other, preferably in combination with 1,6-hexamethylenediamine (NMDA).

Typically, the microcapsules formed according to an embodiment of this invention have a size range of 0.2 microns to 30 microns. Preferably, the microcapsules are in a size range of from 1 micron to 15 microns and more preferably, the microcapsules have a size range of from 2 microns to 10 microns.

A further embodiment of the invention relates to preparing the water-dispersible granular composition which involves spray drying the aqueous suspension of microcapsules containing the agrochemical active ingredient within a polymeric shell wall.

The aqueous microcapsule suspension of the agrochemical active ingredient is mixed and blended with a filler base which is added to the aqueous suspension of microcapsules.

The filler base includes, at least one water insoluble filler, and at least one water soluble suspension adjuvant.

The water insoluble fillers used typically include one or more of microcrystalline cellulose, clays, gums, silicon dioxide, insoluble metal oxides, mineral earths, bentonite, perlite, talc, kaolin, aluminium silicate, diatomaceous earth, attapulgite, barium sulfate, mica, calcium carbonate, fused sodium potassium, precipitated silicates, aluminium silicate, zeolites and mixtures thereof. The water insoluble fillers are present in a concentration range of from 2% to 60% by weight, preferably from 5% to 20% by weight of the total composition.

The filler base further includes a water soluble suspension adjuvant. The water soluble suspension adjuvant included in the filler base particularly aids in enhancing the stability of the water dispersible granular composition. The water soluble suspension adjuvant also improves the physical properties of the formulation.

According to another embodiment, the water soluble suspension adjuvant is used in about 1% to about 25% of the total composition. Preferably, the water soluble suspension adjuvant is used in about 1% to about 10% of the total composition. In fact, it is observed that using higher amounts of the water soluble suspension adjuvant in the filler base may a negative effect on the physical properties including suspensibility.

According to an embodiment, the water soluble suspension adjuvant includes one or more of water soluble starches, water soluble carbohydrates, polyvinylpyrrolidones and mixtures thereof. The carbohydrates include mono, di or oligosaccharides. The carbohydrates particularly include glucose, fructose, sucrose, trehalose, lactose, dextrose, maltose, galactose, mannose and mixtures thereof.

According to another embodiment, the oligosaccharides include dextrins such as maltodextrin, amylodextrin, cyclodextrin compounds and their derivatives.

The filler base further includes at least one at least one agrochemical excipient. The agrochemical excipient can include one or more of anionic surfactants and one or more salts or derivatives of ligninsulfonate.

The anionic surfactants typically include alkyl sulfate salts, polyoxyethylene alkyl ether sulfate salts, polyoxyethylene alkyl phenyl ether sulfate salts, polyoxyethylene styryl phenyl ether sulfate salts, alkylbenzene sulfonate salts, alkylsulfosuccinate salts, naphthalene sulfonate salts, alkylnaphthalene sulfonate salts, salts of formalin condensate of naphthalene sulfonic acid, fatty acid salts, polycarboxylate salts, N-methyl-fatty acid sarcosinate, resinates, polyoxyethylene alkyl ether phosphate salts, polyoxyethylene alkyl phenyl ether phosphate salts, salts of alkylnaphthalene sulfonic acid-formalin condensate and mixtures thereof. The anionic surfactants are present in the filler base in the concentration of from 0.5% to 50% by weight of the composition, preferably from 1.0% to 30% by weight and most preferably from 5% to about 25% by weight.

The filler base further includes salts or derivatives of lignosulfonates which include water soluble salts such as sodium lignosulfonate, potassium lignosulfonate, magnesium, calcium or ammonium lignosulfonate, and mixtures thereof.

The sodium salt of lignin sulfonate is preferably used. Any commercially available lignin sulfonate salt which does not contain added surfactant, may be conveniently used. Commercially available lignin sulfonates which may be mentioned are: Treax®, LTS, LTK and LTM, respectively, the potassium, magnesium and sodium salts of lignosulfonate (50% aqueous solutions); Marasperse CR® and Marasperse CBOS-3®, sodium lignosulfonate, and Marasperse C21®, calcium sulfonate, Reed Lignin Co., Polyfon O®, Polyfon T®, Reax 88B®, Reax 85B®, sodium salts of lignin sulfonate, Westvaco Polychemicals and Borresperse NA (registered trademark of Borregaard LignoTech). The lignosulfonates are present in a concentration range from 2% to 60% by weight of the total composition, preferably from 10% to 30% by weight of the total composition.

Additionally, one or more of agrochemical excipients such as surfactants, dispersing agents, wetting agents, diluents, emulsifiers and binders may be added to the spray dispersion. The spray dispersion can further optionally include one or more water soluble salts, antifoaming agents, antifreeze agents, stabilizers, if required, or other agents used in the formation of the water dispersible granule formulation.

The dispersing agents that can be used include ionic or non-ionic agent or a mixture of such surface-active agents. The dispersing agents typically include polycarboxylates, naphthalene sulfonate condensates, phenol sulfonic acid condensates and methyl oleyl taurates or mixtures thereof. The wetting agents typically include sulfosuccinates, naphthalene sulfonates, sulfated esters, phosphate esters, sulfated alcohol and alkyl benzene sulfonates.

The emulsifiers that can be used should be compatible with the liquid active substance and with the other components of the formulation. The emulsifiers can be of the anionic, cationic or non-ionic type. The emulsifiers are selected from a group comprising ethoxylated and ethopropoxylated alcohols and nonyl phenols, ethoxylated tristeryl phenol, ethoxylated tristeryl phenol phosphates, ethoxylated and ethopropoxylated castor oil, calcium alkyl benzene sulfonates and proprietary blended emulsifiers. These emulsifiers are usually used in admixture. The actual ratio varies depending on the liquid active. However, those skilled in the art will appreciate that it is possible to utilize other agrochemical excipients known in the art, without departing from the scope of the invention.

Optionally, water soluble salts that can be used include inorganic salt, such as chlorides, nitrates or sulfates of ammonium or an alkali metal salt or an alkaline earth metal salt, such as sodium, potassium, calcium, zinc, copper, manganese or magnesium.

The water dispersible granular composition may also contain other biologically active agents that are not encapsulated.

The dispersion obtained is then spray dried in a suitable spray drying or spray granulation apparatus to obtain the water dispersible granular composition. The spray drying of the microcapsule dispersion is carried out under typical spray-drying conditions, in which the inlet temperatures of the spray drying apparatus, is generally in the range from about 105 to about 200 degree C. and the outlet temperature ranges from about 45 to about 95 degree C. Temperatures in excess of these may cause fusing of particles in the agglomerate which is detrimental to spontaneity and redispersion of the water-dispersible granule in water. The temperature of the water-dispersible granule coming out of the tower should be below a temperature at which the shell wall would fuse.

The filler base and the optional excipients function to cause agglomeration of the microcapsules during the spray drying process, when water is removed from each droplet emanating from the spray nozzle and an aggregate is formed containing many small microcapsules associated together with a fine layer of the filler base homogenously interspersed between each microcapsule. The filler base thus functions by both separating the microcapsules from each other while also agglomerating the microcapsules to each other, into larger granules which are readily dispersible in water.

The filler base and the excipients create such a bridge between the microcapsules within the granules and between the granules themselves to aid in preventing fusion, caking and attrition, during manufacture and storage. The filler base subsequently facilitates the disassociation of the water-dispersible granules, when it is added to water to form a spray suspension. It is surprisingly seen that the water dispersible granular composition including the filler base exhibits tremendously improved physical characteristics of suspension and dispersion, when the water dispersible granular composition is added to water. The filler base further protects the integrity of the microcapsules during the drying stage, or during storage, thereby enhancing the storage stability of the water dispersible granular composition even at elevated temperatures. Not only this, it is surprising to note that the careful selection and combination of various aspects of the water soluble suspension adjuvant in the microcapsule and the careful selection of the various elements of the filler base, provide a composition which demonstrates a better biological efficacy, and allows the user to use the formulation at a reduced dosage of the active ingredient.

The water dispersible granules formed have a particle size in the range of 0.1 micron to 50 microns, preferably 0.1 micron to 20 micron, more preferably 0.1 microns to 12 microns. Most preferably, the water dispersible granules formed have particles in the size range of 0.1 microns to 10 microns.

The moisture content of the water-dispersible granules obtained is within a range of about 0.1% to 8% and, preferably, no more than 4%. Most preferably, the moisture content of the water dispersible granules is within the range of 1% to 2%.

Typically, the water dispersible granular composition will not generally release the agrochemical active ingredient until after application to the desired target. Alternatively, the water dispersible granular composition may be designed to release the agrochemical active ingredient slowly over a period of time.

According to an embodiment, the invention further relates to a method of application of the water dispersible granular composition to the crops, soil or the seeds. The composition may be applied through a variety of methods. The composition may be sprayed directly to the plant, such as its foliage or applied to the plant propagation material, before it is sown or planted, or to the locus thereof. Methods of applying to the soil can be via any suitable method, which ensures that the composition penetrates the soil, for example, nursery tray application, in furrow application, soil drenching, soil injection, drip irrigation, application through sprinklers or incorporation into the soil, and such other methods.

The rates of application or the dosage of the composition depends on the type of use, the type of crops, or the specific active ingredients in the composition but is such that the agrochemical active ingredient, is in an effective amount to provide the desired action (such as disease or pest control).

Surprisingly, it is observed that the water dispersible granular composition of the invention is effective at reduced dosages of application, for the control of large number of insects, primarily the sucking and the chewing insects, found in agricultural and plantation crops in particular, but may also be effectively used in other places infected with undesired insects.

The water-dispersible granules of the invention immediately exhibit excellent dispersion when added to water, wherein the large aggregates dissociate or break apart into the tiny, individual microcapsules which disperse to their original pre-agglomerated form throughout the water. Further, since the pesticide is encapsulated, one can get a high degree of loading of the active ingredient, upto about 80% of the active ingredient, as compared to the prior art compositions. Further the structure and the composition of the water-dispersible granules permit them to be free flowing and relatively dust-free. Moreover, since the agrochemical active ingredient is encapsulated, the water-dispersible granules of the invention pose very little hazard to the user at the time of application.

The present invention will be illustrated in more detail with reference to the following formulation examples and test examples. As will be recognized by one skilled in the art, these examples are just illustrative and are not meant to be limiting.

A. FORMULATION EXAMPLES

The following examples illustrate the basic methodology and the versatility of the invention.

Example 1

Preparation of Water Dispersible Granules Containing Microcapsules of 24% Lambda Cyhalothrin (C1)

25.5 parts of molten lambda Cyhalothrin technical (96% purity) was dissolved in 10 parts of the solvent GR 110 and the solution was heated at 55° C.-60° C. To this solution, 3 parts of Poly methylene diphenyl diisocyantes (PMDI) was added under stirring to obtain the oil phase. An aqueous phase was prepared by mixing 6 parts of Gohensol GL 03 solution with 34 parts water in a homogenizing vessel and heating the mixture to 55° C.-60° C. 38.5 parts of the oil phase was added drop-wise to the aqueous phase, under high shear mixing at 55° C.-60° C. 16 parts of 5% Diethylene triamine solution were then added and the mixture was kept under stirring for 5 mins. The reaction mixture was cooled to room temperature. About 2 parts of 33% solution of Citric acid was added to the reaction mixture to bring the pH to 6.5 and obtain a microencapsulation suspension. 52 parts of filler base including 14 parts of Terrsperse 2020, 25 parts of Sodium Lignosulphonate, 5 parts of finely grounded Clay mix, 5 parts of Hydroxypropyl betacyclodextrin and 3 parts of alkyl naphthalene sulfonate (Supragil WP) were added to 48 parts of water to prepare a filler base slurry. 97 parts of the microencapsulation suspension were added to the filler base slurry under mixing to obtain a spray dispersion. The dispersion was spray granulated in a granulating apparatus with an inlet temperature of around 120° C. and an outlet temperature of around 70° C. to obtain the water dispersible granular composition. The composition had the following particle size distribution of 0.1 to 5 microns wherein: D10: 0.8 microns, D50: 1.6 microns, D90: 3.1 microns.

TABLE 1

| Sr. No. | Constituent | Weight % |
| --- | --- | --- |
| 1 | Lambda cyhalothrin | 27.2 |
| 2 | PMDI | 3.2 |
| 3 | Solvent GR 110 | 10.7 |
| 4 | Gohensol GL 03 | 6.4 |
| 5 | Diethylene triamine | 0.9 |
| 5 | Antifoam | 0.2 |
| 7 | Citric acid | 0.7 |
| 8 | Alkyl Naphthalene Sulphonate sodium salt (Terrsperse 2020) | 13.6 |
| 9 | Sodium Lignosulphonate | 22.7 |

TABLE 1-continued

| Sr. No. | Constituent | Weight % |
|---|---|---|
| 10 | Alkyl naphthalene sulfonate (Supragil WP) | 2.9 |
| 11 | China Clay | 6.5 |
| 12 | Hydroxypropyl betacyclodextrin | 5.0 |
|  | Total | 100 |

Example 2

Preparation of Water Dispersible Granules Containing Microcapsules of 24% Cypermethrin (C2)

A composition as detailed in Table 2 was prepared according to the method provided in Example 1 with 25.5 parts of Cypermethrin technical. Hydroxypropyl betacyclodextrin in the filler base was replaced with 5 parts of sucrose. The composition had the following particle size distribution: D10: 0.6 microns, D50: 2.75 microns, D90: 5.0 microns.

TABLE 2

| Sr. No. | Constituent | Weight % |
|---|---|---|
| 1 | Cypermethrin | 26.0 |
| 2 | PMDI | 3.1 |
| 3 | Solvent GR 110 | 10.2 |
| 4 | Gohensol GL 03 | 6.1 |
| 5 | Diethylene triamine | 0.8 |
| 6 | Antifoam | 0.2 |
| 7 | Citric acid | 0.7 |
| 8 | Alkyl Naphthalene Sulphonate sodium salt (Terrsperse 2020) | 14.3 |
| 9 | Sodium Lignosulphonate | 23.76 |
| 10 | Alkyl naphthalene sulfonate (Supragil WP) | 3.0 |
| 11 | China Clay | 6.84 |
| 12 | Sucrose | 5.0 |
|  | Total | 100.0 |

Example 3

Preparation of Water Dispersible Granules Containing Microcapsules of 20% Propaquizafop with Maltodextrin in the Filler Base (C3)

A composition similar to Example 1 was prepared with 25.5 parts of Propaquizafop technical (96% purity). Hydroxypropyl betacyclodextrin in the filler base was replaced with 5 parts of maltodextrin. The details of the composition are as set forth in the Table below: The composition had the following particle size distribution: D10: 0.6 microns, D50: 4.75 microns and D90: 8.94 microns.

TABLE 3

| Sr. No. | Constituent | Weight % |
|---|---|---|
| 1 | Propaquizafop | 21.9 |
| 2 | PMDI | 2.6 |
| 3 | Solvent GR 110 | 8.6 |
| 4 | Gohsenol GL 03 | 5.2 |
| 5 | Diethylene triamine | 0.7 |
| 6 | Antifoam | 0.2 |
| 7 | Citric acid | 1.1 |

TABLE 3-continued

| Sr. No. | Constituent | Weight % |
|---|---|---|
| 8 | Alkyl Naphthalene Sulphonate sodium salt (Terrsperse 2020) | 15 |
| 9 | Sodium Lignosulphonate | 28.995 |
| 10 | Alkyl naphthalene sulfonate (Supragil WP) | 3.0 |
| 11 | China Clay | 7.705 |
| 12 | Maltodextrin | 5.0 |
|  | Total | 100.0 |

Example 4

The table below demonstrates comparative data of the physical properties of Suspensibility and Storage stability of the water dispersible granular composition comprising microcapsules of 24% Lambda cyhalothrin, initially and after 14 days of storage at 54 degree Celcius.

Suspensibility is defined as the amount of active ingredient suspended after a given time in a column of liquid, of stated height, expressed as a percentage of the amount of active ingredient in the original suspension. Suspensibility is the ability of the granules to stay suspended upon dilution in water.

Dispersibility is a property of water dispersible granule formulations, which is the ease with which the granules disperse when added to water. Thus, it is always desirable to have a water dispersible granule formulation that not only disperses spontaneously, but also remains suspended upon dilution for a continuous period of time.

Test for Suspensibility:

A suspension of known concentration in standard water or distilled water is prepared, placed in a prescribed measuring cylinder at a constant temperature, and allowed to remain undisturbed for the specified time. The top 9/10th are drawn off and the content of active ingredient in the bottom 1/10th determined, so allowing the content of the top 9/10th to be calculated.

TABLE 4

| Sample | Initial Suspensibility | Suspensibility After ATS at 54° C. (14 days) |
|---|---|---|
| C1 | 100 | 85 |
| C2 | 100.0 | 85.6 |
| C3 | 97.9 | 86 |
| C4 | 95.9 | 78 |
| C5 | 83 | 60.0 |
| C6 | 93 | 65 |

C1, C2 and C3 are water dispersible granular compositions containing microcapsules of 24% Lambda cyhalothrin, 24% Cypermethrin and 20% Propaquizafop, respectively, prepared as per the embodiments of the invention, and as set forth in Examples 1, 2 and 3, wherein the filler base includes 5% Hydroxypropyl betacyclodextrin, 5% sucrose and 5% maltodextrin, respectively.

C4 are water dispersible granular compositions containing microcapsules of 24% Lambda cyhalothrin prepared as per an embodiment of the invention, wherein the filler base includes 5% polyvinylpyrrolidone.

C5 is a water dispersible granular composition containing microcapsules of 24% Lambda cyhalothrin, prepared as per the teaching in U.S. Pat. No. 6,419,942. The composition included lamba cyhalothrin, an aromatic Solvent (Solvesso 200) in the microcapsules. The filler base included lignin sulfonate, xanthan gum; an anionic surfactant (Witconate 90) and polyvinyl Alcohol (Airvol 203).

C6 is a water dispersible granular composition containing microcapsules of 24% Lambda cyhalothrin, with the microcapsules containing Lamba cyhalothrin, an aromatic Solvent (Solvesso 200) and Gohensol GL-05, a Polyvinyl Alcohol with a molecular weight of from 22,000 to 32,000, a degree of hydrolysis a viscosity of from 5.2 cps to 6.2 cps. The filler base included lignosulfonate, an anionic surfactant (Witconate 90) and water soluble salt (sodium citrate) and a water insoluble filler (Clay).

It is observed that the samples C1 and C2 exhibited an initial suspensibility of 100%. C3 also showed an initial suspensibility of 97.9%. It was surprisingly observed that C1, C2 and C3 prepared according to the embodiments of the invention, showed a suspensibility as high as 85%, 85.6% and 86% respectively, even under storage for 14 days at high temperatures, as compared to the sample C5 (prepared according to the teaching of the '942 patent, not including the water soluble suspension adjuvant in the filler base). It was in fact observed that the sample C5 (prepared as per the teaching of the '942 patent), which did not include a water soluble suspension adjuvant, exhibited a very poor suspensibility of 64% after 14 days of storage at a higher temperature. C4 prepared as the per the embodiments of the invention, including polyvinylpyrrolidone in the filler base also showed a good suspensibility of 78% after 14 days of storage under accelerated conditions. It was further observed that C6 which did not include water soluble suspension adjuvants in the filler base demonstrated a very poor suspensibility of 65% respectively.

It is important that a water dispersible granule formulation not only disperses well, but also remains suspended for an extended period of time, and at higher temperatures, in order to ensure uniform application of the active ingredient.

It is to be noted that a suspensibility of at least 70% is desirable and a suspensibility of less than 70% does not pass the tests of the registration procedure at the various international regulatory authorities, for instance, the US Environmental Protection Agency (US EPA), the Central Insecticide Bureau (CIB), India; the Institute for the Control of Agrochemicals, Ministry of Agriculture (ICAMA), China and the European Commission (EC), Europe.

It can be therefore concluded from the observations that the compositions as per the embodiments of the invention exhibit enhanced physical properties of suspension and storage stability as compared to the prior art compositions, even under accelerated storage conditions at high temperatures.

Example 5

Formulations of water dispersible granules comprising microcapsules encapsulating active ingredients with higher water solubilities:
  a. Thiamethoxam, a neonicotinoid insecticide is a crystalline powder with a melting point of 139.1° C., having a high solubility in water of 4100 mg/liter. When attempting to prepare water dispersible granules comprising microcapsules of Thiamethoxam as per an embodiment of this invention, it was observed that Thiamethoxam was not soluble in the solvent C-9. It is observed that thiamethoxam decomposed immediately beyond its melting point. On attempting to add methylene diphenyl diisocyanate (MDI) in molten Thiamethoxam, it polymerized immediately due to high temperature. Thus Thiamethoxam could not be microencapsulated and it was not possible to prepare its water dispersible granular formulation.

b. Propoxur, a carbamate insecticide is a white crystalline solid with a melting point of 90° C. with a water solubility of 1800 mg/liter. A water dispersible granular composition comprising microcapsules of 25% Propoxur within a polyurea shell wall with Gohensol GL-03 was made, according to an embodiment of the invention, including maltodextrin as a water soluble suspension adjuvant in the filler base, along with clay, sodium lignosulfonate and alkyl naphthalene sulfonate (Supragil WP). The suspensibility observed was 85%. A water dispersible granule composition comprising microcapsules of 25% Propoxur was prepared with the microcapsules having a polyurea shell wall and polyvinyl alcohol Gohensol GL-03. The filler base contained ligninsulphonate, sodium citrate, an alkyl naphthalene sulphonate (Supragil WP) and clay (excluding the water soluble suspension adjuvant). It was observed that the suspensibility of the water dispersible granular composition was observed to be 93%.

Field Studies:

Table 5 below demonstrates the superior control of the *Thrips* population with the application of the compositions according to the embodiments of the invention.

Trials were laid in Nashik-Lasalgaon in the state of Maharashtra, India, to evaluate various compositions including Lambda cyhalothrin against *Thrips* in Onion. The plots size was 9 m². All the recommended agronomic practices were followed. Single sprays of each treatment were applied with the help of knapsack sprayer. Observations of number of *thrips* per onion plant were made before and after 1 hr, 5 hrs, 1 day, 5 days and 7 days of spraying.

Treatments Applied:

TABLE 5

| Treatment | Products | Dose Per Acre (gms) | Dosage of Active Ingredient per Acre (gms) | Dose per 1000 sq mt. (gm/ml) |
|---|---|---|---|---|
| T1 | C1 | 35 | 8.4 | 8.75 |
| T2 | C1 | 42 | 10.08 | 10.5 |
| T3 | LAMBDA 5 EC | 200 ML PER ACRE | 10 | 50 |
| T4 | LAMBDA 4.9 CS | 200 ML PER ACRE | 9.8 | 50 |
| T5 | C5 | 45 | 10.8 | 11.25 |
| T6 | CONTROL | | | |

T1 and T2 are treatments with water dispersible granular compositions containing microcapsules of 24% Lambda cyhalothrin prepared as per the embodiments of the invention, applied at a dosage of 8.4 gms and 10.08 gms of active ingredient, per acre.

T3 is a treatment with Lambda cyhalothrin 5% Emulsifiable Concentrate

T4 is a treatment with Lambda cyhalothrin 4.9% Capsulated Suspension

T5 is a treatment with a water dispersible granular composition containing microcapsules of 24% Lambda cyhalothrin prepared as per the teaching of the '942 patent applied at a dosage of 10.8 gms of active ingredient, per acre.

T6 is Control.

Test Results:

TABLE 6

| Treatment | | Dosage | | Observation DAT | | | | |
|---|---|---|---|---|---|---|---|---|
| Treatment | Quantity Used/ Acre | of Active ingredient per Acre (gms) | Before Spray (Number of Thrips per plant) | 1 Hour | 5 Hours | 24 Hour | 5 DAT | 7 DAT |
| T1 | 35 gms | 8.4 | 30 to 40 (about 3-4 are adult) | 5% Immobility | 15% Immobility | 80% Immobility & 50 Mortality % | 80% Immobility & 50% Mortality | 68% Immobility & 45% Mortality |
| T2 | 42 gms | 10.08 | | 20% Immobility | 20% Immobility & 15% Mortality | 90% Immobility & Mortality 55% | 90% Immobility & Mortality 55% | 80% Immobility & Mortality 50% |
| T3 | 200 ML EC | 10 | | 5% Immobility | 10% Immobility | 60% Immobility & 40% Mortality | 70% Immobility & 40% Mortality | 60% Immobility & 37% Mortality |
| T4 | 200 ML CS | 9.8 | | No Effect | 5% Immobility | 30% Immobility | 30% Immobility & Mortality 28% | 30% Immobility & 22% Mortality |
| T5 | 45 gms | 10.8 | | No Effect | 5% Immobility | 35% Immobility | 32% Immobility & Mortality 28% | 32% Immobility & Mortality 25% |
| T6 | Control | | | | | Infestation is same | Infestation increased to Avg of 45 to 50 Thrips per plant | Farmer took the spray of Lambda Cyhalothrin 5% on 22nd Dec i.e 7 DAT |

Immobility Relates to Slowing Down of *Thrips*

It was observed that the treatment 72, with a composition as per an embodiment of the invention, shows exceptionally good control of the *Thrips* population, with 50% mortality, even after 7 days of spraying, as compared to the treatments T3 and T4 (known emulsifiable concentrate (EC) and microcapsule formulation (CS) respectively) which showed a reduced mortality after 7 days of spraying. It was also observed with the treatment T2, that 80% of the *Thrips* population was rendered immobile, even after 7 days of spraying, as compared to treatments T3 and T4 which showed a poor reduction in the mobility of the *Thrips* population.

The treatment T2 was also effective as compared to the treatment T5 (prepared as per the teaching of the '942 patent) which showed a poor control as can be noted from the results in the above table, after 7 days of treatment.

Further T1 (prepared as per an embodiment of the invention) showed a highly effective control in terms of mortality and reduction in mobility of the *Thrips* population, at a reduced dosage of upto 22.2% as compared to the treatment T5. Also, it was surprisingly observed that treatment T1, applied at a substantially reduced dosages of 16% and 14.67%, as compared to the treatment T3 and T4 respectively, showed an effective control even after 7 days of treatment. 14 in fact, exhibited an extremely poor control of the *Thrips* population. Thus it is surprising to note that water dispersible granular compositions as per the embodiments of the invention (T1 and T2) showed better performance at a lower dosages as compared to the known EC or CS formulations, let alone prior art water dispersible granules. Further, the treatments T1 and T2 showed an immediate effect within an hour of its application and it was observed that the effect sustained over an extended period of time, as compared to the known EC and CS formulations as well the prior art water dispersible granules. This is a truly surprising effect, as EC and CS formulations typically have a better biological field performance as compared to a water dispersible granule formulation. The surprising effects are due to unique combination of the constituents in the formulation of the present invention, which provides a stable and free flowing water dispersible granule with excellent physical properties, excellent release of the microencapsulated active, and a fine particle size distribution.

Thus, it can be concluded that the water dispersible granular compositions, according to the embodiments of the invention show significantly enhanced bioefficacy, as compared to conventional CS and EC formulations and other prior art water dispersible granule formulations, even at reduced dosages of application with an effect sustained over a longer duration of time.

Besides, being chemically stable for a prolonged period of time, even under storage at higher temperatures, the compositions exhibit enhancement in the physical properties such as suspensibilty. This ensures a uniform application of the composition on the target area, rendering the composition extremely effective for spray application, whereby the composition is highly effective at reduced dosages of application. At the same time, use of large amounts of hazardous organic solvents is eliminated with the use of the composition of the invention, which renders the composition not only environment friendly but also user friendly, with an improved toxicological profile with reduced eye and skin irritation.

From the foregoing, it will be observed that numerous modifications and variations can be effectuated without departing from the true spirit and scope of the novel concepts of the present invention. It is to be understood that no limitation with respect to the specific embodiments illustrated is intended or should be inferred.

I claim:

1. A water dispersible granular composition consisting essentially of:
   i. microcapsules comprising:
      a. at least one agrochemical active ingredient encapsulated within a polymeric shell wall; and, wherein the agrochemical active ingredient has a water solubility of less than 100 mg/liter; and,
      b. polyvinyl alcohol with a molecular weight of from 15,000 to 21,000, a degree of hydrolysis of from 87% to 89% and a viscosity of from 3.5 cps to 4.5 cps;
   ii. a filler base consisting essentially of:
      a. at least one water insoluble filler;
      b. at least one water soluble suspension adjuvant selected from the group consisting of water soluble carbohydrates and polyvinylpyrrolidone; and,
   iii. at least one agrochemical excipient.

2. The water dispersible granular composition of claim 1, wherein the agrochemical active ingredient comprises at least one of an insecticide, a fungicide, a herbicide, an acaricide, a nematicide, a pheromone, a plant growth regulator and mixtures thereof.

3. The water dispersible granular composition of claim 1, wherein the agrochemical active ingredient is a pyrethroid.

4. The water dispersible granular composition of claim 3, wherein the pyrethroid is selected from one or more of lambda cyhalothrin, cypennrmethrin, bifenthrin and permethrin.

5. The water dispersible granular composition of claim 1, wherein the agrochemical active ingredient is one or more of aryloxyphenoxypropionic herbicides.

6. The water dispersible granular composition of claim 1, wherein the agrochemical excipient comprises one or more anionic surfactants.

7. The water dispersible granule composition of claim 1, wherein the agrochemical excipient comprises one or more salts or derivatives of a ligninsulphonate.

8. The water dispersible granular composition of claim 1, wherein the water insoluble filler comprises one or more of microcrystalline cellulose, clays, gums, silicon dioxide, insoluble metal oxides, mineral earths, bentonite, perlite, talc, kaolin, aluminium silicate, diatomaceous earth, attapulgite, barium sulfate, mica, calcium carbonate, fused sodium potassium, precipitated silicates, zeolites and mixtures thereof.

9. The water dispersible granular composition of claim 1, wherein the water soluble suspension adjuvant is present in a concentration range of from 1% to 10% of the total composition.

10. The water dispersible granular composition of claim 6, wherein the anionic surfactant is selected from one or more of alkyl sulfate salts, polyoxyethylene alkyl ether sulfate salts, polyoxyethylene alkyl phenyl ether sulfate salts, polyoxyethylene styryl phenyl ether sulfate salts, alkylbenzene sulfonate salts, alkylsulfosuccinate salts, naphthalene sulfonate salts, alkylnaphthalene sulfonate salts, salts of formalin condensate of naphthalene sulfonic acid, fatty acid salts, polycarboxylate salts, N-methyl-fatty acid sarcosinate, resinates, polyoxyethylene alkyl ether phosphate salts, polyoxyethylene alkyl phenyl ether phosphate salts, salts of alkylnaphthalene sulfonic acid-formalin condensate and mixtures thereof.

11. The water dispersible granular composition of claim 1, wherein the granule comprises a second agrochemically active ingredient which is not encapsulated.

12. A process of preparing the water dispersible granular composition as claimed in claim 1, wherein, the process comprising the steps of:
   a. dissolving at least one active ingredient with a water solubility of less than 100 mg/liter and at least one first monomer to obtain an organic phase;
   b. homogenizing polyvinyl alcohol with a molecular weight of from 15,000 to 21,000, a degree of hydrolysis of from 87% to 89% and a viscosity of from 3.5 cps to 4.5 cps with water in a homogenizer to obtain an aqueous phase;
   c. mixing the organic phase, the aqueous phase and at least one second monomer under high shear mixing and stirring to obtain a microencapsulation suspension;
   d. adding an aqueous suspension comprising water and a filler base including at least one water insoluble filler; at least one water soluble suspension adjuvant; and, at least one agrochemical excipient; to the microencapsulation suspension of step c to obtain a spray dispersion; and,
   e. spray drying the spray dispersion to obtain the water dispersible granular composition.

13. A method of treatment of a plant comprising applying to the plant, plant propagation material or locus thereof, the composition as claimed in claim 1.

* * * * *